United States Patent [19]
Wang et al.

[11] Patent Number: 5,210,180
[45] Date of Patent: May 11, 1993

[54] ENCHANCEMENT OF PORCINE SOMATOTROPIN ACTIVITY

[75] Inventors: Bosco S. Wang, Cranbury; Ian C. Hart, Pennington, both of N.J.; Hong-Ming Shieh, Langhorne, Pa.

[73] Assignee: American Cyanamid Company, Stamford, Conn.

[21] Appl. No.: 427,669

[22] Filed: Oct. 27, 1989

[51] Int. Cl.$^5$ .................. A61K 37/02; C07K 1/00
[52] U.S. Cl. ..................................... 530/328; 530/345
[58] Field of Search .............. 530/327, 328, 399, 345; 514/5, 15

[56] References Cited

U.S. PATENT DOCUMENTS

| 4,452,775 | 6/1984 | Kent | 424/19 |
| 4,857,637 | 8/1989 | Hammonds et al. | 530/403 |

FOREIGN PATENT DOCUMENTS

| 104920 | 4/1984 | European Pat. Off. |
| 111389 | 6/1984 | European Pat. Off. |
| 137234 | 4/1985 | European Pat. Off. |
| 284406 | 9/1988 | European Pat. Off. |
| 303972 | 2/1989 | European Pat. Off. |
| WO89/00166 | 1/1989 | PCT Int'l Appl. |
| 8901490 | 2/1989 | World Int. Prop. O. |

OTHER PUBLICATIONS

Krivi et al. Mol. Immun. vol. 23 No. 12, 1381 (1986).
Rudinger et al. "Peptide Hormones" (J. A. Parsons–ed.) Jun. 1976 1–6.
Retegui et al. Endocrin 111 No. 2 668–676 (Aug. 1982).
Pena et al. Molec. Immun. Biol. 17 1487–1491 (1980).
Ferrara et al. Eur. J. Immun. 9 1020–1023 (1979).
Abdel-Mequid et al. J. Mol. Biol. 192 159–160 (1986).
Dictionary–Biochem & Molec Biol. (2nd ed) (Wiley & Sons 1989) at 222.
Abdel-Meguid, S. S. et al., Proc. Natl. Acad. Sci., 84, 6434–6437 (1987).
Groesbeck, M. D., and Parlow, A. F., Endocrinology, 120, 2582–2590 (1987).

Primary Examiner—Merrell C. Cashion, Jr.
Assistant Examiner—Bennett Celsa
Attorney, Agent, or Firm—Alan M. Gordon

[57] ABSTRACT

This invention is directed to peptide fragments of porcine somatotropin (pST) which are used to generate epitope-specific anti-pST antibodies. When such antibodies are administered with pST to warm-blooded animals, the growth enhancing activity of pST is potentiated.

3 Claims, 16 Drawing Sheets

ENCHANCEMENT OF PORCINE SOMATOTROPIN ACTIVITY

FIELD OF THE INVENTION

This invention relates to the identification of three peptide fragments of porcine somatotropin (pST) that may be used to generate anti-pST antibodies. When these antibodies are administered together with pST, animal growth is improved beyond that achieved with the administration of pST alone.

BACKGROUND OF THE INVENTION

The growth hormone pST is native to swine and accounts for maturation of the animal, including increasing the growth rate and the lean to fat ratio. Endogenous amounts of pST are small; therefore, efforts have focused on the preparation of exogenous pST for use in large-scale agriculture.

One aspect of those efforts has been the determination of the complete amino acid sequence of pST. It has been found that pST is a single chain polypeptide of 191 amino acids with two cystine bridges linking residues 53-164 and 181-189, respectively (Abdel-Meguid, S.S., et al., *Proc. Natl. Acad. Sci.*, 84, 6434-6437 (1987)).

Efforts have also been directed to the identification of peptides which consist of small portions of the amino acid sequence of somatotropin of various species with a view to enhancing the activity of these growth hormones. Published European Patent Application 137,234 describes the cleavage of a 7 kd fragment from the C-terminal end of human growth hormone (hGH). Mice were injected with the fragment; the mice then generated antibodies to the fragment. Those antibodies were administered to mice in combination with hGH. It was found that mice receiving hGH plus antibodies to the hGH fragment exhibited greater growth than those receiving hGH alone.

Published European patent application 284,406 describes the preparation of a fragment corresponding to amino acid residues 35-53 of pST. The pST fragment was administered to pigs and anti-pST antibodies were generated. A similar experiment was carried out with a fragment of bovine somatotropin (bST). In the latter case, the anti-bST antibodies so generated were then administered together with intact bST and were found to enhance the activity of bST.

SUMMARY OF THE INVENTION

Although the work of others described above has provided information about certain regions of somatotropin of various species, including porcine, that enhance the growth-promoting activity of such hormones, these investigations have not provided data about other possible fragments of the hormones which may contain epitopic sites, nor have comparative data been presented comparing the growth-enhancing activity of antibodies to such fragments.

Accordingly, it is an object of this invention to identify additional fragments of pST which, when administered to warm-blooded animals, generate antibodies to pST. Such pST fragments include peptides having amino acid sequences homologous to the following portions of pST: 98-110, 110-118 and 155-163.

It is a further object of this invention to improve growth by treating warm-blooded animals with antibodies generated by such pST fragments in combination with pST. Such antibodies may be polyclonal or monoclonal.

It is yet another object of this invention to administer antibodies generated by such pST fragments to warm-blooded animals and to measure growth when those animals are thereafter treated with pST. Such pST may have either a native or modified amino acid sequence, so long as its growth enhancing function is present.

It is still another object of this invention to compare the enhancement of animal growth resulting from the administration of pST together with antibodies from different pST fragments. The invention is also directed to amino acid sequences which are the antigenic equivalents of these pST fragments, as well as to antibodies therefrom.

These objects are accomplished in the description of the invention set forth below.

DETAILED DESCRIPTION OF THE INVENTION

Figure 1:
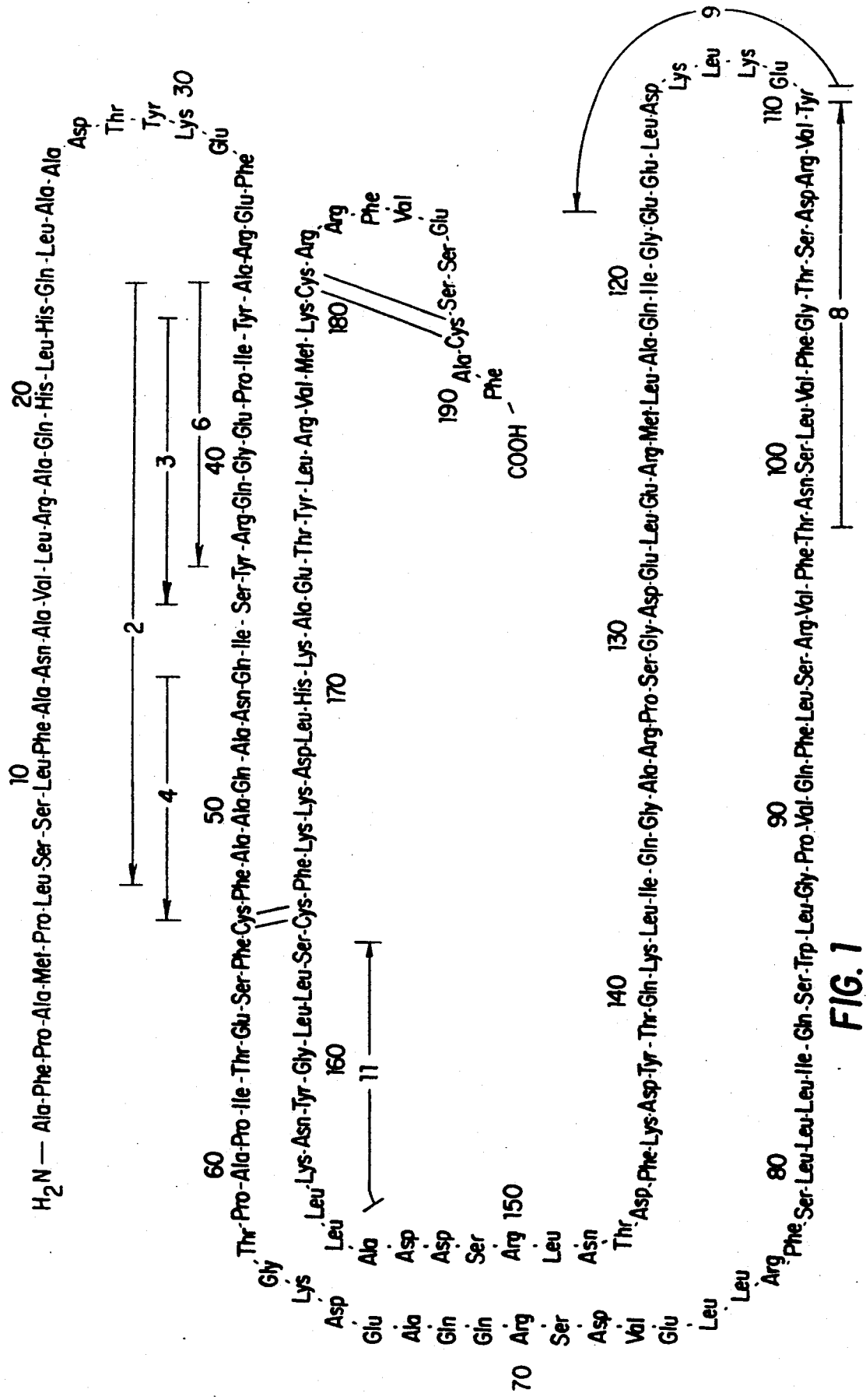
FIG. 1 depicts the amino acid sequence of pST and seven peptide fragments of pST, including peptides designated 8, 9 and 11 which are the subject of this invention.

This invention is directed to the identification of antigenic epitopes of pST, in the form of peptide fragments which are capable of inducing immunologic responses in warm-blooded animals through the generation of epitope-specific anti-pST antibodies. Such antibodies are then administered together with pST to animals to enhance their growth performance. Alternatively, these antibodies are administered to animals which are thereafter treated with pST.

The three pST peptides of this invention are designated by numbers and their amino acid sequences (aa) are as follows:

8 (aa 98–110): Thr-Asn-Ser-Leu-Val-Phe-Gly-Thr-Ser-Asp-Arg-Val-Tyr
9 (aa 110–118): Tyr-Glu-Lys-Leu-Lys-Asp-Leu-Glu-Glu
11 (aa 155–163): Leu-Leu-Lys-Asn-Tyr-Gly-Leu-Leu-Ser.

These three peptides have amino acid sequences which are homologous to the corresponding portions of pST.

This invention is also directed to peptides having amino acid sequences which are antigenically equivalent to those just described for peptides #8, 9 and 11. Such peptides may be said to be antigenically equivalent to peptides having amino acid sequences homologous to the corresponding portions of pST if their amino acid sequences differ only by minor deletions from or conservative substitutions to the pST sequences so that the tertiary configurations of the peptides are substantially unchanged from those of the pST portions and antibodies can be generated to those peptides.

For comparison purposes, four other pST peptides are constructed with amino acid sequences based upon those disclosed in European patent application 284,406:

2 (aa 35–52): Ala-Tyr-Ile-Pro-Glu-Gly-Gln-Arg-Tyr-Ser-Ile-Gln-Asn-Ala-Gln-Ala-Ala-Phe
3 (aa 36–44): Tyr-Ile-Pro-Glu-Gly-Gln-Arg-Tyr-Ser
4 (aa 46–53): Gln-Asn-Ala-Gln-Ala-Ala-Phe-Cys
6 (aa 35–43): Ala-Tyr-Ile-Pro-Glu-Gly-Gln-Arg-Tyr

These seven peptides may be constructed by techniques known in the art including, but not limited to, chemical synthesis, use of a solid phase peptide synthesizer and expression by a DNA nucleotide sequence in an appropriate host. The peptides are then purified by suitable means such as gel filtration chromatography and preparative reverse-phase high performance liquid chromatography (HPLC). The purity of the peptides is demonstrated by amino acid composition analysis.

In order to enhance the formation of antibodies in vivo, a peptide of this invention preferably is linked to a macromolecule which functions as a carrier for the peptide. For example, the peptide may be conjugated to a protein such as keyhole limpet haemocyanin (KLH). Other carriers within the scope of this invention include those known in the art such as human and bovine serum albumins, myoglobins, $\beta$-galactosidase, penicillanase and bacterial toxoids. The carriers may also be synthetic molecules such as multi-poly-DL-alanyl-poly-L-lysine and poly-L-lysine.

In one embodiment of this invention, polyclonal antibodies to these peptides are generated and purified from immunized warm-blooded animals such as swine and rabbits. In another embodiment of this invention, monoclonal antibodies to these peptides may be prepared using conventional techniques.

Polyclonal antibodies are generated by immunizing animals with the peptides of this invention, either alone or in conjugated form. The peptides may be administered by conventional routes such as subcutaneous injection, intramuscular injection and intravenous flow, as well as transdermal and oral administration. It is preferred to administer the peptides (or their conjugates) in association with a carrier containing an adjuvant, such as Freund's complete adjuvant. It is particularly preferred to use a dosage regimen where an initial administration of the peptides is followed by one or more booster administration of the same peptides at regular time intervals.

Polyclonal antibodies are recovered by first obtaining a blood sample from an immunized animal after a time sufficient from administration of the peptide for antibodies to be formed. The serum (which contains the antibodies) is isolated by conventional means such as centrifugation. Serum is separated into fractions containing immunoglobulin (Ig) and lacking immunoglobulin (non-Ig) by means such as fast protein liquid chromatography (FPLC). Only the Ig fraction contains antibodies to the peptides. The antibodies are then isolated from the Ig fraction by SDS-PAGE. The purity of the antibodies so isolated is greater than 98% as determined by SDS-PAGE. The antibody titer level is assayed using enzyme-linked immunosorbent assay (ELISA) according to conventional procedures.

Monoclonal antibodies are prepared by immunizing mice with one of the three novel pST peptides, removing the spleens of the mice, preparing suspensions of lymphocytes, fusing these lymphocytes to mouse myeloma cells, culturing the cells and collecting supernatants of surviving hybridomas for antibody screening by solid-phase ELISA. Those hybridomas which produce desired antibodies are further subcloned and injected in mice. Ascites are then collected from the mice and Ig is purified by ammonium sulfate precipitation or a protein A affinity column on FPLC. Samples of Ig so purified are assayed against antigens using ELISA to identify the antibodies formed.

These antibodies (polyclonal and monoclonal) may be used in two ways to potentiate and enhance the growth-promoting activity of pST. First, an antibody is administered to a warm-blooded animal together with pST. Alternatively the animal is treated with one or more doses of an anti-pST antibody and is subsequently treated with pST. In either procedure, more than one antibody may be used. Thus, the invention also contemplates the administration of combinations of anti-pST antibodies #8, 9 and 11 or their antigenic equivalents.

The biological activity of these antibodies is tested in hypophysectomized (hypox) rats. Hypox-rats are growth-deficient as a result of surgical removal of their pituitary glands. Hypox-rats serve as a useful model for studying the effect of somatotropin on growth (Groesbeck, M. D. and Parlow, A. F., *Endocrinology*, 120, 2582-2590 (1987).

Treatment of these hypox-rats with a combination of pST and antibodies to the peptides of the present invention enhances the growth-promoting effect of pST. The pST used may be isolated from natural sources or may be prepared using recombinant techniques such as those described in published European patent applications 104,920 or 111,389. The sources of and the method of isolation/preparation of pST itself forms no part of this invention. The antibodies may also be used together with recombinant pST in which the amino acid sequence of native pST has been modified using a technique such as site-directed mutagenesis, so long as the growth enhancing function of pST is present. See, for example, co-pending, commonly-assigned U.S. Ser. No. 372,699, filed Jul. 3, 1989; see also published European patent application 303,972.

The immunoreactivity of antibodies to pST peptides is examined in swine and rabbits. As shown in Tables 2 and 3 below, most antibodies generated by these peptides are found to be rather specific to their respective antigens. However, antibody to peptide #2 (aa=35-52) and #8 (aa=98-110) in swine and peptide #3 (aa=36-44) in rabbits appears to possess a broad spectrum of immunoreactivity. This effect as to peptides #2 and #3 might be explained by the overlaps of the amino acid sequences of peptide #2 (aa=35-52) and #3 (aa=36-44). Cross reactivity of anti-peptide #6 (aa=35-43) antibody with peptide #2 (aa=35-52) in both species might be due to the same possibility. It is not clear why peptide #8 (aa=98-110) induces antibody with multiple specificities in swine, while failing to generate antibody recognizing all peptides being tested in rabbits. It is noteworthy that all antibodies induced by peptides recognize pST, whereas anti-pST antibody is not reactive with peptides, except peptide #2 in rabbits. As expected, normal animals produce no antibody to pST and its fragments.

Figure 4:
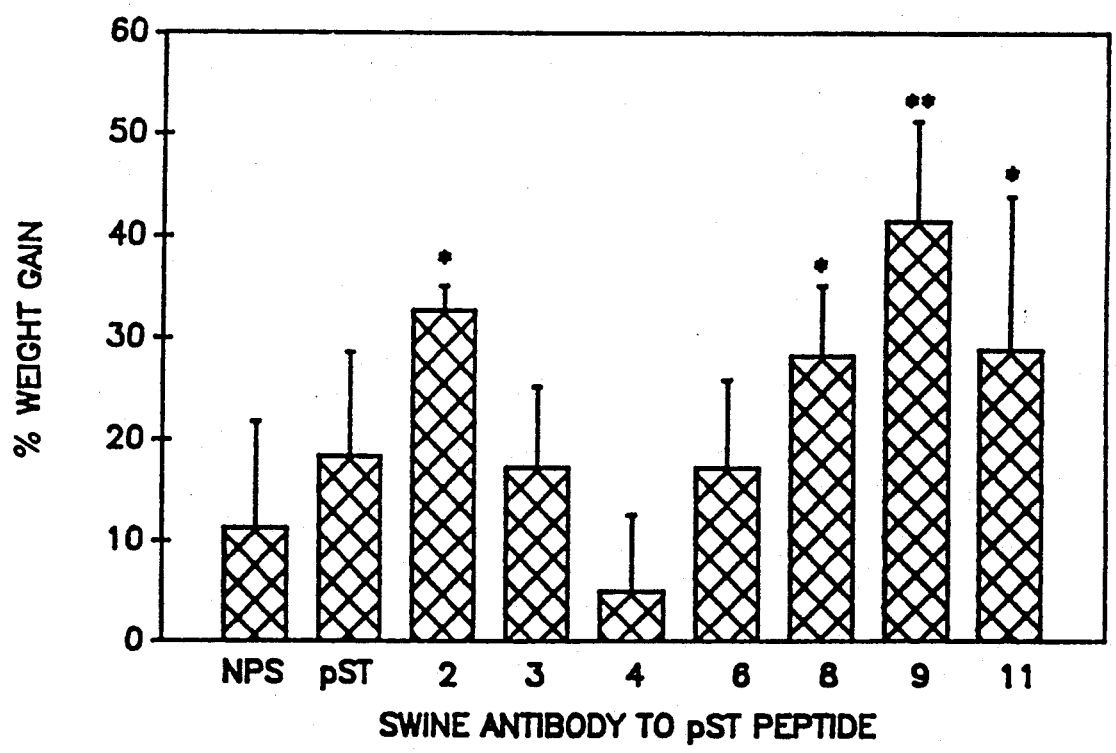
FIG. 4 depicts the effect on the growth of hypophysectomized rats treated with pST alone or pST in combination with swine antibodies to pST peptides. Normal porcine serum (NPS), which contains small amounts of endogenous pST, is used as a negative control.

Daily treatment of hypox-rats with pST markedly restores their ability to grow. The somatogenic effect is potentiated when pST is administered together with the antibodies to the pST peptides described previously (see FIGS. 4 and 5). Such antibodies have pST epitope-specificity. These antibodies not only heighten the effect but also accelerate the action of pST (see FIGS. 7A, 7B and 7C).

Findings from a series of experiments (shown in FIGS. 4 and 5) demonstrate that swine antibodies to peptide #2 (aa=35-52), #8 (aa=98-110), #9 (aa=110-118) and #11 (aa=155-163) potentiate pST growth enhancement activity. However, these antibodies are not effective when administered in the absence of pST. Furthermore, normal swine Ig (NPS), anti-pST antibody and antibodies to peptides #3 (aa=36-44), #4 (aa=46-53) and #6 (aa=35-43) have no statistically significant effect. The dose response studies shown in FIGS. 6A, 6B and 6C indicate that the action of antibodies to peptides #8, 9, and 11 is rapid and exhibits a bi-phasic dose response curve.

The growth-promoting swine antibodies include those responding to pST amino acid sequences of 35-52, 98-110, 110-118 and 155-163. Each of these antibodies is not active when employed in the absence of pST; they require pST for enhancement of activity. Their action is rather rapid and also exhibits a bi-phasic dose response curve.

Figure 9:
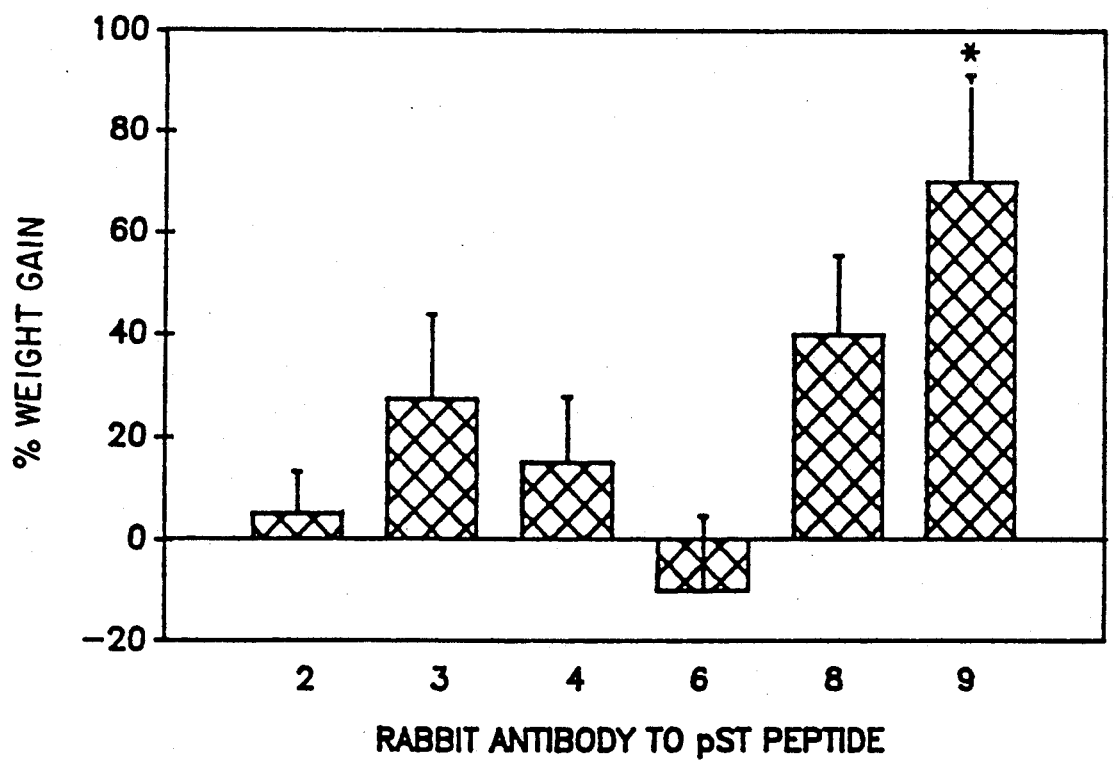
FIG. 9 depicts the effect on the growth of hypophysectomized rats treated with pST alone or pST in combination with rabbit antibodies to pST peptides.
Figure 10:
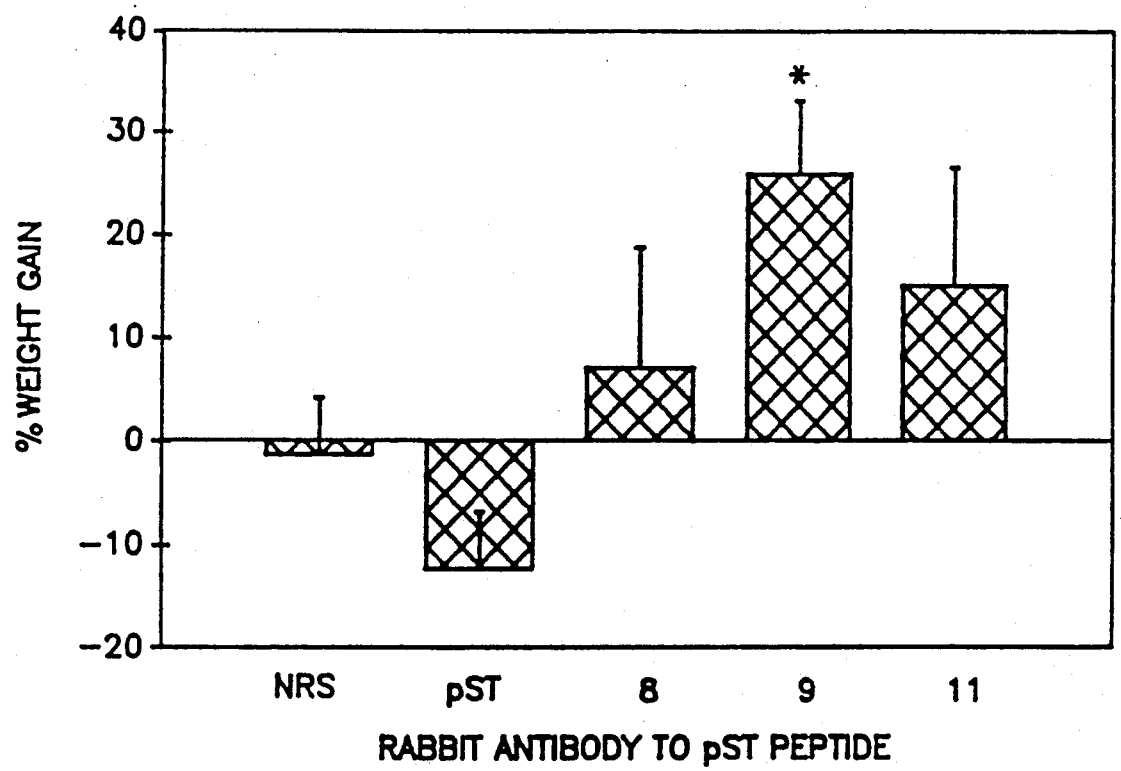
FIG. 10 depicts the effect on the growth of hypophysectomized rats treated with pST alone or pST in combination with rabbit antibodies to pST peptides in an experiment separate from depicted in FIG. 9. Normal rabbit serum (NRS), which contains small amounts of endogenous rabbit somatotropin, is used as a negative control.

Rabbit antibodies are tested in a similar manner (FIGS. 9 and 10). Only the antibody responding to the pST amino acid sequence of 110-118 (peptide #9) significantly potentiates the effect of pST. Taken together, the present findings indicate that antibodies with certain pST epitope specificities are capable of enhancing the somatogenesis of pST. However, anti-peptide #2 (aa=35-52), #8 (aa=98-110) and #11 (aa=155-163) antibodies from rabbits fail to duplicate the effect seen with swine antibodies.

Although the mechanism of action of these antibodies is not clear, applicants suggest several possible mechanisms. Without being bound by theory, the mechanisms may be as follows: 1) prolongation of the half-life time of somatotropin in circulation, 2) improvement of somatotropin delivery to liver cells, 3) increase of somatotropin uptake efficiency by polymerization on target cell surface, 4) lengthening the somatotropin interaction with receptors by retardation of internalization process (endocytosis), 5) restriction of somatotropin effects towards somatogenesis, and 6) alteration of somatotropin configuration better suitable for interacting with growth-related receptors.

Applicants' results suggest that possibilities 1-4 are less likely to be the case because, despite the fact that all tested antibodies react immunologically with pST, only a few enhance the growth-promoting effect of pST. Further support for the statement in the preceding sentence is provided by the fact that antibody raised against the intact pST molecule is highly reactive with pST, yet shows no growth-enhancing effect. On the other hand, attachment of antibodies to certain regions of the pST molecule may alter the conformation and such a reorientation may make it better presented to appropriate receptors.

This application presents an approach to improve growth performance in the animal production industry. Active immunization of livestock with certain pST peptides which contain antigenic epitopes, such as aa=98-110, aa=110-118 and aa=155-163, leads to the generation of antibodies in host animals. These antibodies amplify the somatogenic activity of endogenous or exogenous somatotropin. Alternatively, these novel peptides and antibodies can also be used to induce anti-idiotypic antibodies by means of conventional techniques. Such anti-idiotypic antibodies may prove useful as potential vaccines.

In order that this invention may be better understood, the following examples are set forth. The example is for the purposes of illustration only and is not to be construed as limiting the scope of the invention.

EXAMPLE 1

1. Preparation Of pST Peptides

Peptides are synthesized manually or by a Biosearch 9600 (Miligen Biosearch, Burlington, Mass.) solid phase peptide synthesizer. Amino acids linked to an N-t-butyloxycarbonyl (Boc) protecting group, namely, Boc-Ala, Boc-Gly, Boc-Val, Boc-Leu, Boc-Pro, Boc-Ser (OBzl), Boc-Thr (OBzl), Boc-Asp (OBzl), Boc-Tyr (2-BrZ), Boc-Arg (Tos), Boc-Lys (2-Clz), Boc-Asn (Xan), Boc-Gln (Xan), and Boc-Cys (4-MeBzl) are purchased from Advanced Chemtech, Louisville, Ky., and employed for synthesis. A Merrifield resin (1% cross-linked divinyl benzene-styrene, Bachem Bioscience Inc., Philadelphia, Pa.) is used as the solid support. The assembled peptide is cleaved from the resin using 95% hydrofluoric acid and 5% anisole at 0° C. for one hour. All peptides are purified by a filtration column with G-25 gel (Pharmacia, Piscataway, N.J.) and preparative reverse-phase HPLC ($C_{18}$ column, acetonitrile/water containing 0.1% TFA, using a gradient of 0% to 90% acetonitrile over 45 minutes).

Figure 2:
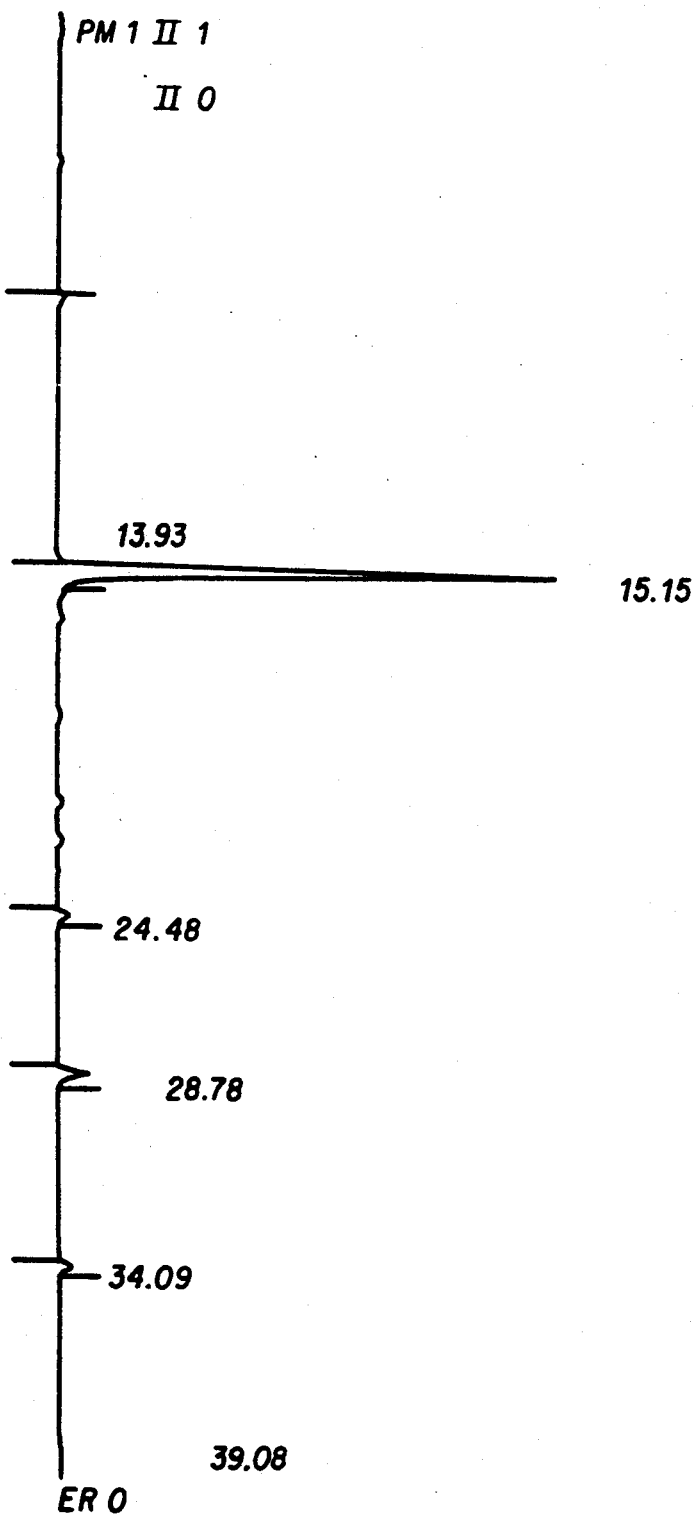
FIG. 2 depicts the purity of peptide #8 as shown by analytic high performance liquid chromatography.

The purity of these peptides is determined by analytical HPLC and an amino acid analyzer. An example of the HPLC analysis is presented for peptide #8 (aa=98-110) in FIG. 2. The major peak in FIG. 2 clearly suggests that the purity of peptide #8 is greater than 95%. The quality of the peptides of this invention is further supported by the amino acid composition analysis as indicated in Table 1:

TABLE 1

AMINO ACID ANALYSIS OF pST PEPTIDES

| Amino Acid | Peptide #8 (98-110) | | Peptide #9 (110-118) | | Peptide #11 (155-163) | |
|---|---|---|---|---|---|---|
| | Ther. $V^a$ | Expt. $V^b$ | Ther. V | Expt. V | Ther. V | Expt. V |
| Arg | $1^c$ | 1.00 | $NA^d$ | | NA | |
| Asp | $2^e$ | $1.86^e$ | 1 | 1.00 | 1 | 1.01 |
| Glu | NA | | 3 | 3.10 | NA | |
| Gly | 1 | 1.08 | NA | | 1 | 1.04 |
| Leu | 1 | 1.03 | 2 | 1.92 | 4 | 3.86 |
| Lys | NA | | 2 | 2.00 | 1 | 1.00 |
| Phe | 1 | 0.88 | NA | | NA | |
| Ser | 2 | 2.00 | NA | | 1 | 0.92 |
| Thr | 2 | 1.99 | NA | | NA | |
| Tyr | 1 | 0.85 | 1 | 0.92 | 1 | 0.98 |
| Val | 2 | 1.73 | NA | | NA | |

$^a$Theoretical values
$^b$Experimental values
$^c$mol/mol peptide
$^d$Not applicable
$^e$The value for aspartic acid includes aspartic acid present in the peptide, as well as asparagine which is hydrolyzed to aspartic acid in the course of the amino acid analysis.

The peptides are then lyophilized and stored at −20° C. in a dessicator cabinet until used.

2. Conjugation of pST Peptides with Keyhole Limpet Haemocyanin (KLH)

Peptides are dissolved in phosphate buffered saline (PBS) (GIBCO, Grand Island, N.Y.) and mixed with KLH (Sigma Chemical Co., St. Louis, Mo.) at an approximate molar ratio of 25 to 1. Glutaraldhyde (0.5%) is added as coupling agent and the mixture is incubated at room temperature for 15 to 60 minutes. $NaBH_4$ is subsequently added and the conjugation mixture is dialyzed extensively against PBS. The aggregates are removed by high speed centrifugation (10,000 g) and the concentration is determined by a UV spectrophotometer at a wavelength of 280 nm.

3. Immunization of Animals with pST Peptides

Conjugates of pST peptide-KLH (1 mg) are emulsified with an equal volume of Freund's complete adjuvant (CFA, GIBCO) prior to administration to swine and rabbits. Female crossbred swine (Duroc×Yorkshire×Hampshire), 3-5 months of age, weighing 30-50 kg, are obtained from the breeding colony of American Cyanamid Company, Princeton, N.J. Swine are injected subcutaneously with 0.5 mg of peptide-KLH conjugates at two different sites in the neck area behind the ears. Female and male New Zealand white rabbits, 10-15 weeks of age, weighing 2-3 kg, are obtained from the Skippack Farm, Skippack, Pa. Rabbits are similarly immunized by injecting the conjugates into both hind limbs. All animals are provided repeatedly with booster injections containing the same antigens every four weeks.

4. Preparation of Polyclonal Antibody

Figure 3:
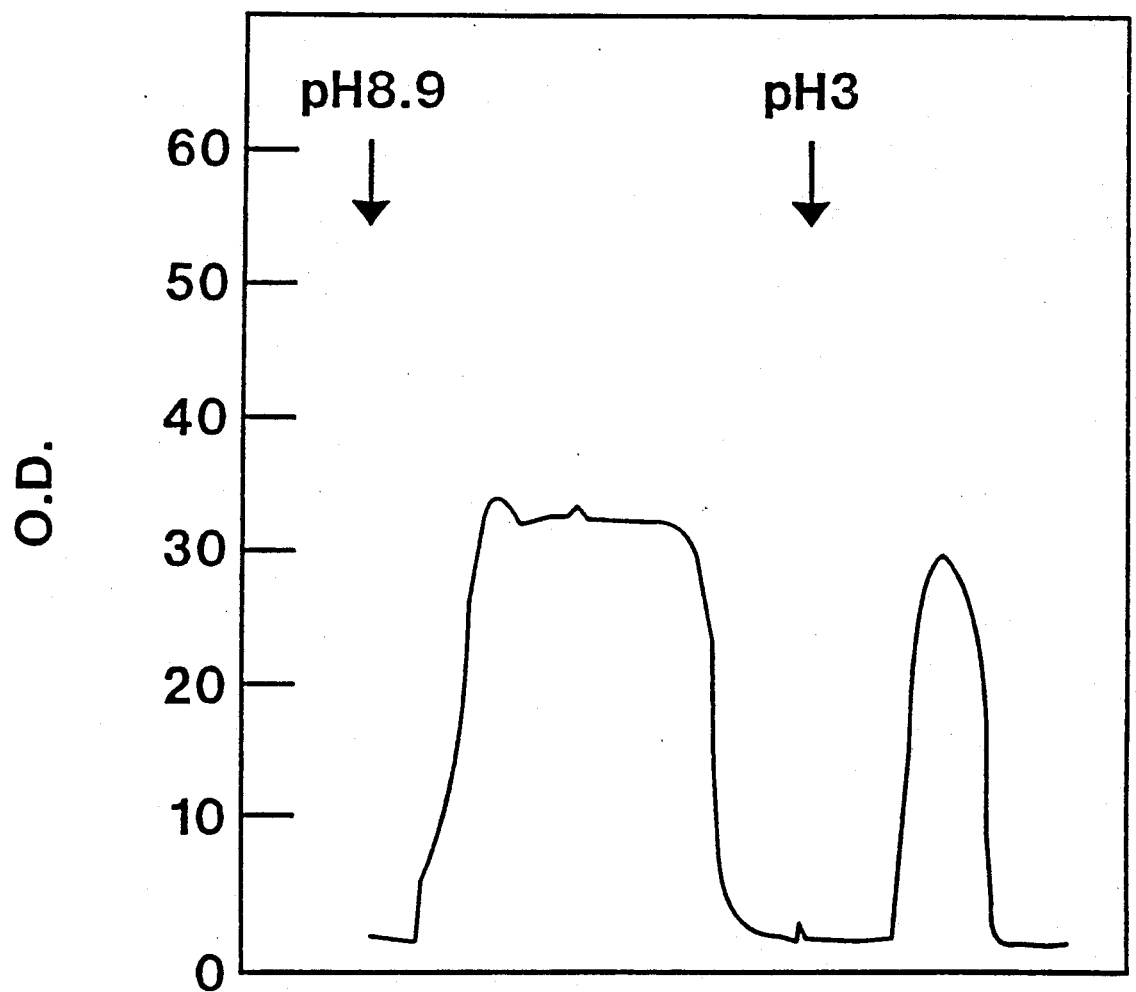
FIG. 3 depicts the purification of the immunoglobulin fraction from serum by the fractionation of serum on a Protein A affinity column.
Figure 3A:
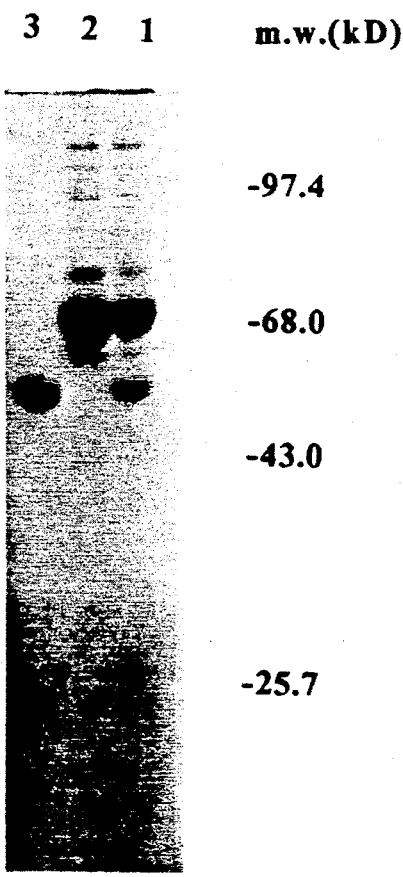
FIG. 3A depicts the purity of the immunoglobulin fraction as shown by sodium dodecyl sulfate-polyacrylamide gel electrophoresis (SDS-PAGE).

Animals are bled 7-14 days after each antigen booster injection. Blood is collected from the jugular vein of swine and the ear vein of the rabbits. After clotting, serum is isolated by centrifugation. All serum samples are diluted to 50% with binding buffer (3M NaCl, 1.5M glycine, pH 8.9) and loaded to a preparative Protein A Superose HR 16/5 column on a FPLC system (Pharmacia, Piscataway, N.J.) in order to purify Ig from serum. The non-Ig fraction is eluted by washing the column with the binding buffer (FIG. 3). The bound Ig fraction is subsequently collected by rinsing the column with 0.1M citric acid, pH 3. It is immediately neutralized to pH 7-8 with 2M Tris buffer, pH 8.2, and concentrated by ultrafiltration (Amicon, Danvers, Mass.). The Ig fraction generally contributes approximately 30% of total serum protein. The purity of the Ig fraction is greater than 98% as determined by SDS-PAGE (FIG. 3A) as follows.

Ig samples are loaded onto a 10% SDS-PAGE slab gel and electrophoresis is performed at 8 mA overnight. The gel is stained with Coomassie blue and protein bands are analyzed by a gel scanner following de-staining. Molecular weight markers include phosphorylase B (97.4 kd), bovine serum albumin (68 kd), ovalbumin (43 kd) and α-chymotrypsinogen (25.7 kd). Following extensive dialysis against PBS, the antibody is aliquoted and stored at −20° C. until use.

5. Solid Phase Enzyme-linked Immunosorbent Assay (ELISA)

Antigen is prepared in PBS and one μg in 100 μl is added to each well of a 96-well flat bottom polystyrene plate. After being incubated for one hour, the plate is washed three times with PBS containing 0.05% Tween-20 by an automatic plate washer (Dynatech Wash II, Chantilly, Va.) and each well is dispensed with 200 μl of 2% BSA (Sigma). The plate is incubated again for another hour. Serum samples are added and tested at a final concentration of 5% in the wells. The plate is incubated for 30 minutes, washed six times with PBS, and added with 100 μl of alkaline phosphatase-conjugated rabbit anti-porcine IgG or goat anti-rabbit IgG F(ab')$_2$ (Zymed Laboratories, South San Francisco, Calif.) at a dilution of 1/1000. The plate is washed again after a 30 minutes incubation and 100 μl of p-nitrophenyl phosphate (1 mg/ml, Sigma) in 0.1M diethanolamine, pH 10.3, is added as substrate for color development. Finally, the colorimetric response is recorded as optical density (OD) by an ELISA plate reader at a wavelength of 405 nm. Incubation procedure is always performed at 37° C.

6. Immunoreactivity Of Antibodies To pST And Its Peptides

Antibodies to pST peptides are generated in swine and rabbits and the immunoreactivity of these antibodies is examined using pST and all seven peptides as target antigens. The bioassay for immunoreactivity is carried out with hypox-rats (female Sprague-Dawley rats, 21 days of age, weighing 50-64 grams each, obtained from the Taconic Farm, Germantown, N.Y.). After being delivered, these rats are kept for observation for 7-10 days to ensure complete hypophysectomy. Using a computer-aided program, animals are randomly allocated to eight rats per group. Two groups of controls are always included in all experiments. The first group consists of untreated hypox-rats which serve as negative controls. The other control group consists of hypox-rats which receive a minimal effective dose of pST (5 μg) by daily injection and thus serve as positive controls. Antibody (0.5 to 1 mg) mixed with 5 μg of pST at room temperature for one hour is administered to each experimental rat. All rats are injected with 0.2 ml test materials subcutaneously at the neck region. The growth of these animals is monitored and recorded as weight gain during the course of the experiment.

The statistical evaluation is carried out by the least-squares analysis of variance for randomized design using the General Linear Models procedure of the Statistical Analysis System. Results of the immunoreactivity tests using antibodies generated in swine are shown in Table 2:

TABLE 2

IMMUNOREACTIVITY OF SWINE ANTIBODIES

| (Antigen)[c] | ANTIBODY TO:[a] | | | | | | | | Normal[b] |
|---|---|---|---|---|---|---|---|---|---|
| | pST | #2 | #3 | #4 | #6 | #8 | #9 | #11 | |
| pST | +++[d] | + | + | + | ++ | + | ++ | + | − |
| #2 (aa 35-52): | − | + | − | − | + | + | − | − | − |
| #3 (aa 36-44) | − | + | + | − | − | + | − | − | − |
| #4 (aa 46-53) | − | − | − | − | − | + | − | − | − |
| #6 (aa 35-43): | − | + | − | − | + | + | − | − | − |
| #8 (aa 98-110): | − | − | − | − | − | + | − | − | − |
| #9 (aa 110-118): | − | + | − | − | − | + | + | − | − |
| #11 (aa 155-163): | − | + | − | − | − | + | − | + | − |

[a]Tested at a dose of 5 μg Ig
[b]From untreated normal swine
[c]1 μg/well
[d]OD readings: "+++" > 1.0; "++" > 0.5; "+" 0.2; "−" < 0.2

The results in Table 2 indicate that swine antibodies raised against various peptides react with their respective antigens, except anti-peptide #4 (aa=46-53) antibody. Antibodies to peptides #2 (aa=35-52) and #8 (aa=98-110) cross-react with almost all antigens being examined, whereas the remaining antibodies are specific. Although all antibodies raised against peptides recognize intact pST, antibody to pST fails to react with any of its peptides. Normal swine Ig is not reactive at all.

Antibodies from rabbits are similarly tested for their immunoreactivity and results are presented in Table 3:

TABLE 3

IMMUNOREACTIVITY OF RABBIT ANTIBODIES

| (Antigen)[c] | ANTIBODY TO:[a] | | | | | | | | Normal[b] |
|---|---|---|---|---|---|---|---|---|---|
| | pST | #2 | #3 | #4 | #6 | #8 | #9 | #11 | |
| pST | +++[d] | ++ | + | ++ | +++ | ++ | + | + | − |
| #2 (aa 35-52): | + | ++ | ++ | − | + | − | − | − | − |
| #3 (aa 36-44): | − | − | ++ | − | − | − | − | − | − |
| #4 (aa 46-53): | − | − | − | − | − | − | − | − | − |
| #6 (aa 35-43): | − | − | ++ | − | +++ | − | − | − | − |
| #8 (aa 98-110): | − | − | ++ | − | − | − | − | − | − |
| #9 (aa 110-118): | − | − | − | − | − | − | +++ | − | − |
| #11 (aa 155-163): | − | − | − | − | − | − | − | +++ | − |

[a]Tested at a final concentration of 0.5%
[b]From untreated normal rabbits
[c]1 μg/well
[d]OD readings: "+++" > 3.0; "++" > 1.0; "+" > 0.5; "−" < 0.5

Peptides #2 (aa=35-52), #6 (aa=35-43), #9 (aa=110-118) and #11 (aa=5-163) induce antibodies recognizing their respective antigens. Antibodies from peptide #6-immunized rabbits weakly cross-react with peptide #2. Antibody generated by peptide #3 (aa=36-44) expresses a broad spectrum of cross-reactivity with peptides #2, #6 and #8. Peptides #4 (aa=46-53) and #8 (aa=98-110) fail to induce any detectable antibody titer to themselves. Although all antibodies recognize the intact pST molecule, pST-induced antibody reacts only with pST, weakly with peptide #2, but not with other peptides.

7. Enhancement of Growth Performance by Swine Antibodies

The growth-promoting effect of antibodies in conjunction with pST is evaluated in hypox-rats. All animals are treated with either 5 μg pST or 5 μg pST together with 1 mg of swine antibody for 10 consecutive days. The body weight is measured and the effect of antibody on pST activity is calculated as percent weight gain over controls who receive pST alone. Results in FIG. 4 demonstrate that antibodies to peptides #2 (aa=35-52), #8 (aa=98-110), #9 (aa=110-118) and #11 (aa=5-163) significantly augment the effect of pST. The remaining antibodies, including normal swine Ig, anti-pST antibody and antibodies to the other peptides, are insignificantly effective.

Figure 5:
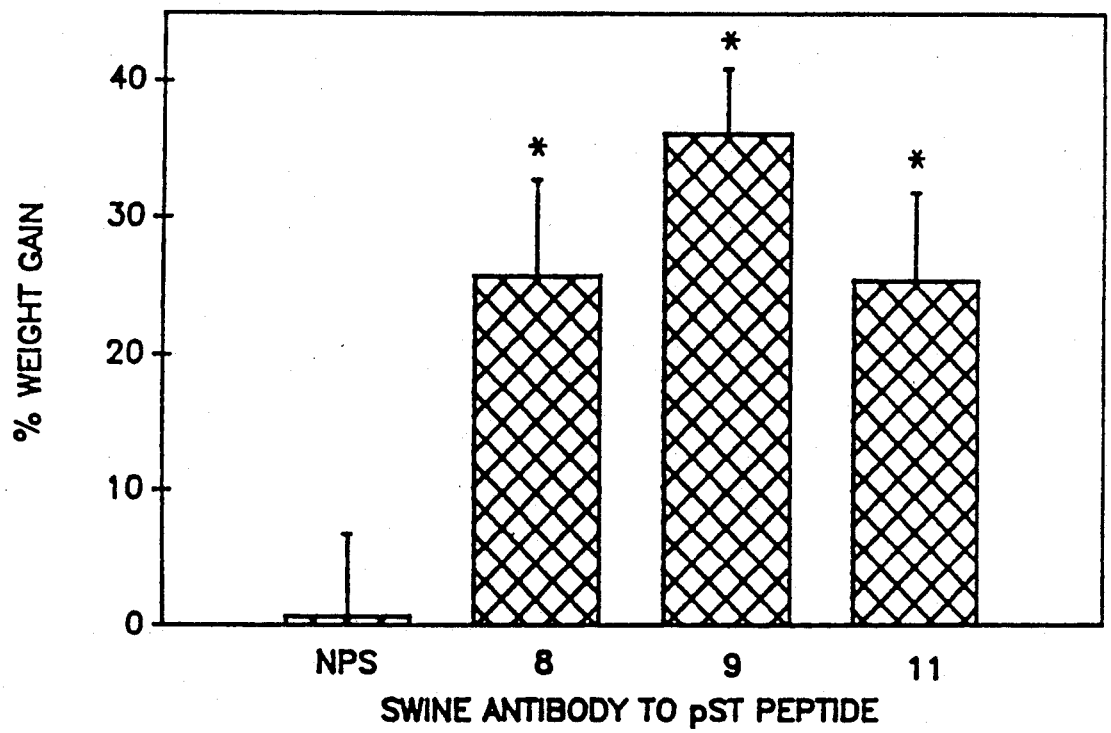
FIG. 5 depicts the effect on the growth of hypophysectomized rats treated with pST in combination with swine antibodies to pST peptides in an experiment separate from that depicted in FIG. 4. The same negative control is used as in FIG. 4.
Figure 6A:
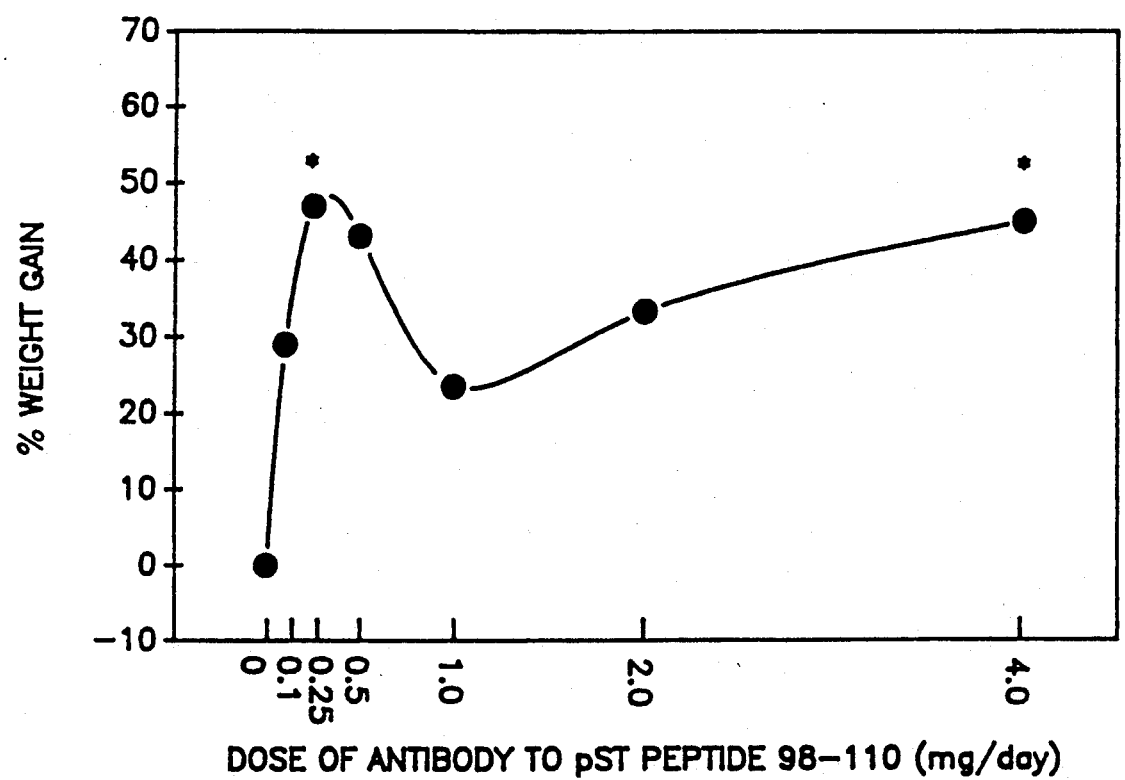
FIG. 6A depicts the dose response of the administration of the swine antibody to pST peptide #8 (amino acids 98-110) plus pST on the growth of hypophysectomized rats.

The effect of antibodies to some of these peptides is retested in a separate experiment and results are presented in FIG. 5. Hypox-rats receive treatments with 5 μg of pST together with antibody to peptides #8 (0.5 mg), #9 (1 mg) and #11 (1 mg) for four consecutive days. The growth of these rats is measured and, again, all three antibodies significantly enhance the effect of pST activity. Normal swine Ig at a dose of 1 mg/day fails to do so.

Figure 6B:
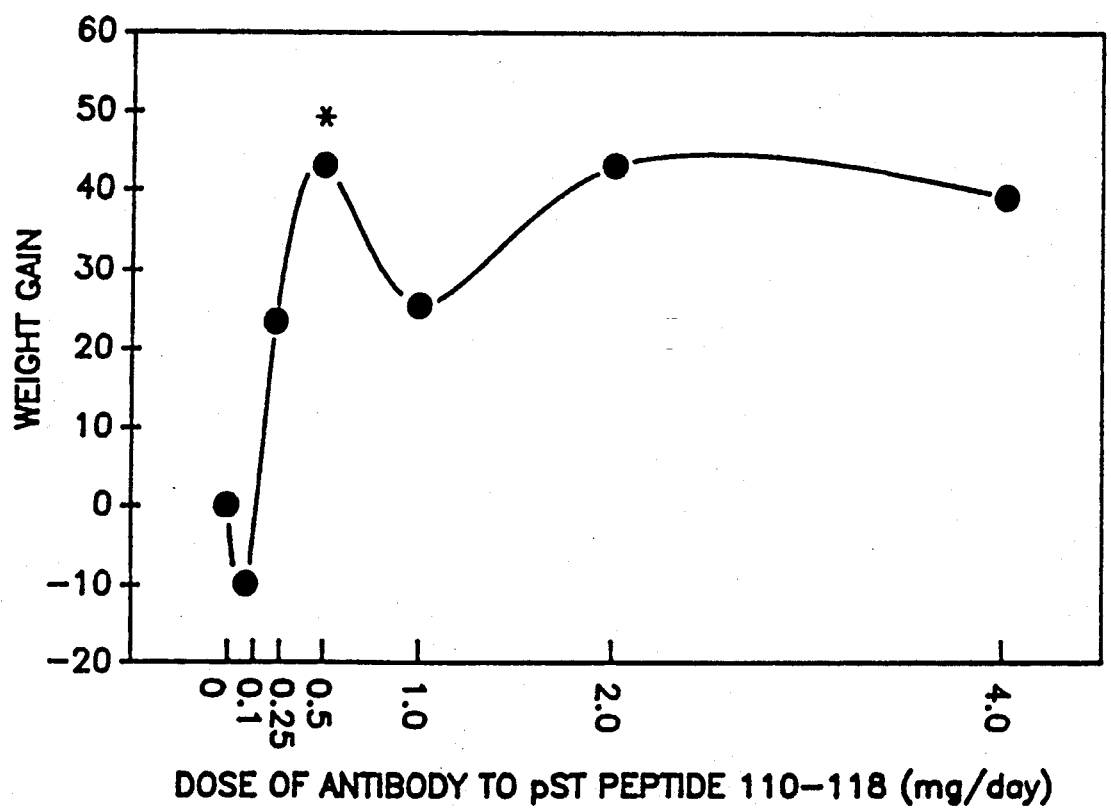
FIG. 6B depicts the dose response of the administration of the swine antibody to pST peptide #9 (amino acids 110-118) plus pST on the growth of hypophysectomized rats.
Figure 6C:
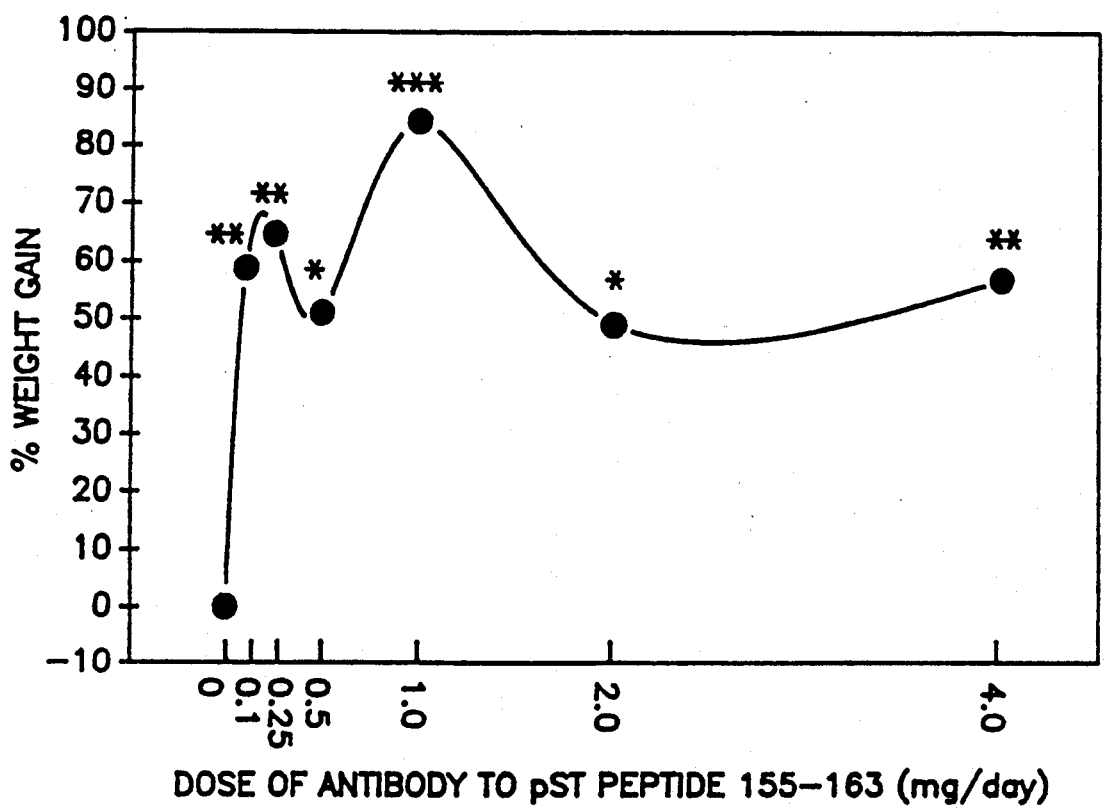
FIG. 6C depicts the dose response of the administration of the swine antibody to pST peptide #11 (amino acids 155-163) plus pST on the growth of hypophysectomized rats.

A dose response study is carried out by treating hypox-rats with various doses of anti-peptide #8 antibody together with 5 μg of pST for four days. Data in FIG. 6A demonstrate that the peak effect of anti-peptide #8 antibody to enhance pST activity is 0.25 mg/day. It declines at the doses of 0.5 to 2 mg/day, but the maximum effect re-appears at 4 mg/day. The biphasic dose response curve is also observed with antibody to anti-peptides #9 and 11. The optimal doses are 0.5 and 2 mg/day for anti-peptide #9 and are 0.25 and 1 mg/day for anti-peptide #11 (FIGS. 6B and 6C, respectively).

Figure 7A:
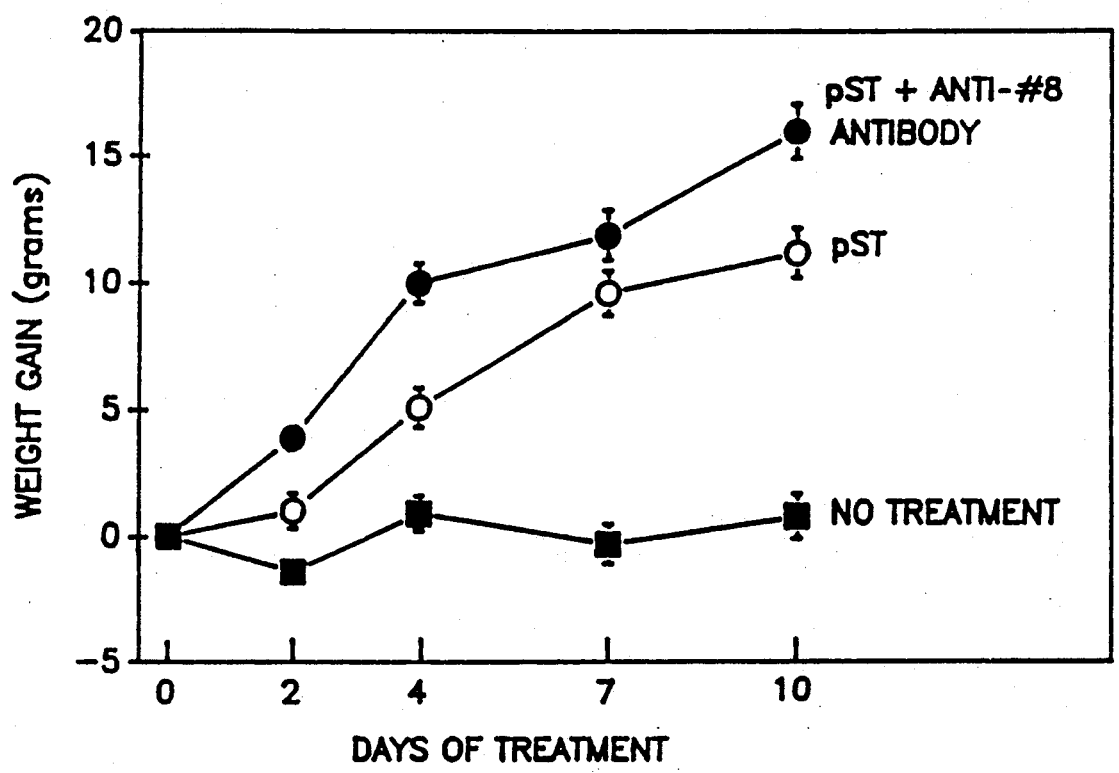
FIG. 7A depicts a time course study comparing the effect on the growth of hypophysectomized rats of treatment with pST alone, pST in combination with the swine antibody to pST peptide #8 (amino acids 98-110) or no treatment.
Figure 7B:
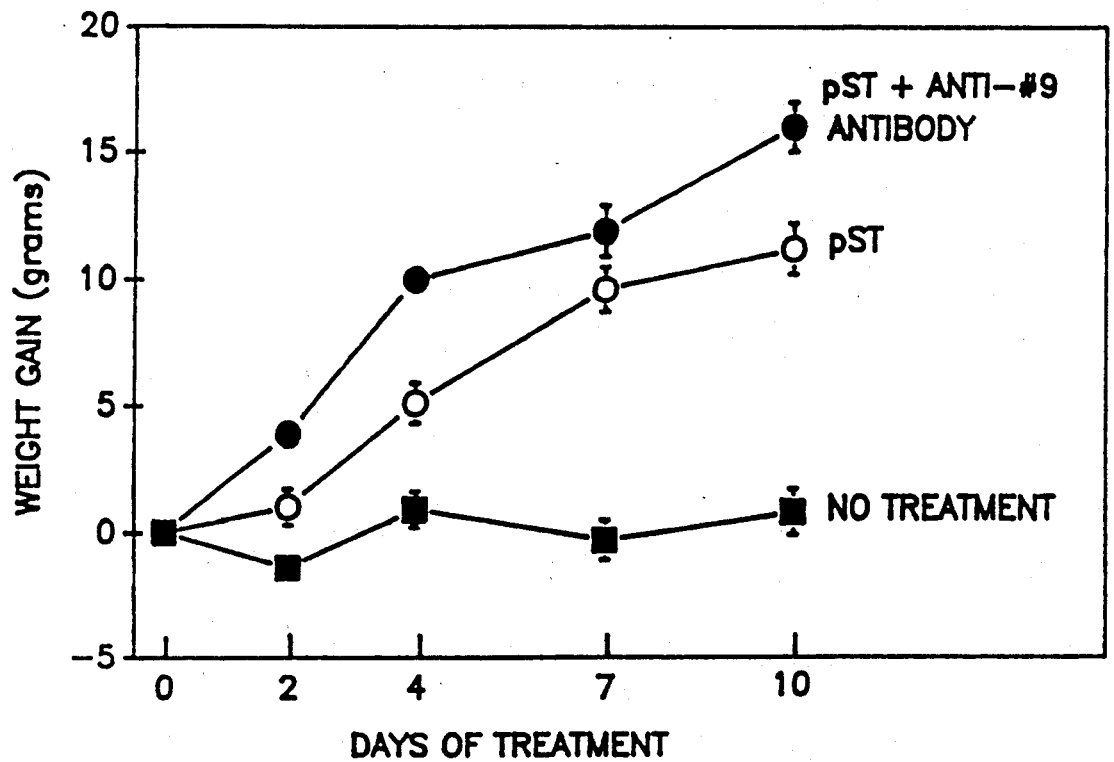
FIG. 7B depicts a time course study comparing the effect on the growth of hypophysectomized rats of treatment with pST alone, pST in combination with the swine antibody to pST peptide #9 (amino acids 110-118) or no treatment.
Figure 7C:
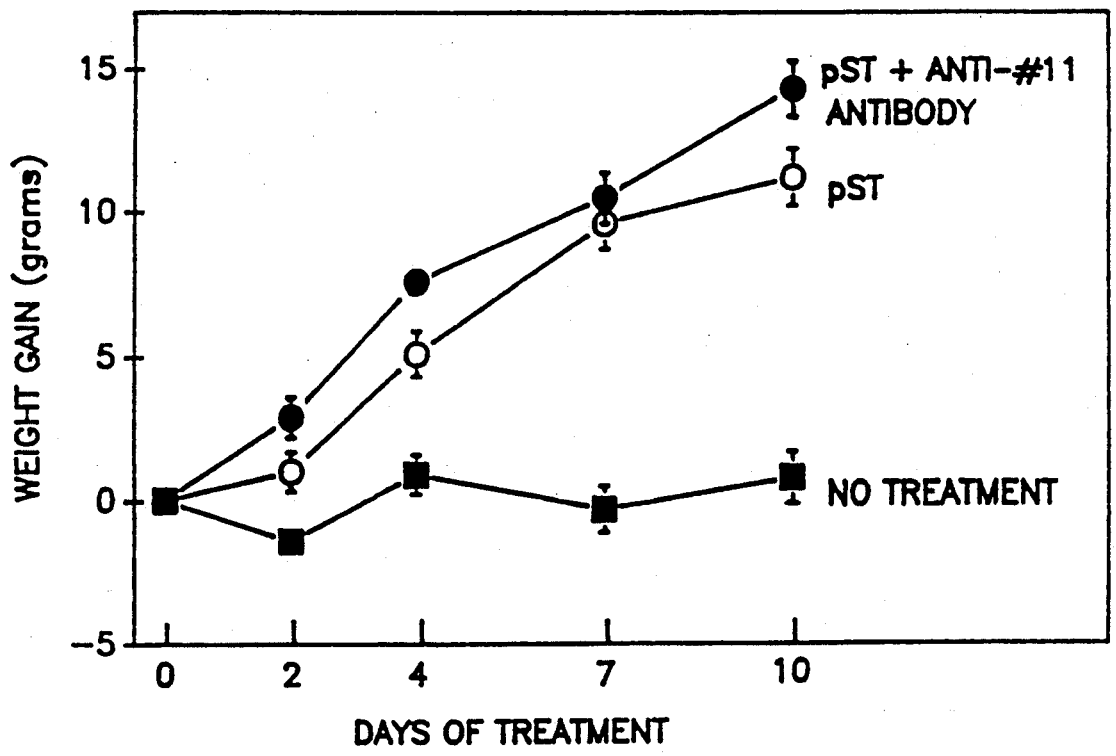
FIG. 7C depicts a time course study comparing the effect on the growth of hypophysectomized rats of treatment with pST alone, pST in combination with the swine antibody to pST peptide #11 (amino acids 155-163) or no treatment.

A time course study on the passive immunization with antibodies to peptides is also investigated. It indicates that hypox-rats have a defect in the normal process of growth (see FIGS. 7A, 7B and 7C; line designated "No Treatment"). However, daily injections with 5 μg of pST for 10 days markedly restore their ability to gain weight. A combination of pST with anti-peptide #8 antibody (0.5 mg/day) further improves the growth performance (FIG. 7A). Significant enhancement by antibody becomes detectable as early as two days after treatment, suggesting a rapid action. Similar observations are also obtained with antibodies to peptides #9 and #11 (see FIGS. 7B and 7C, respectively).

Figure 8:
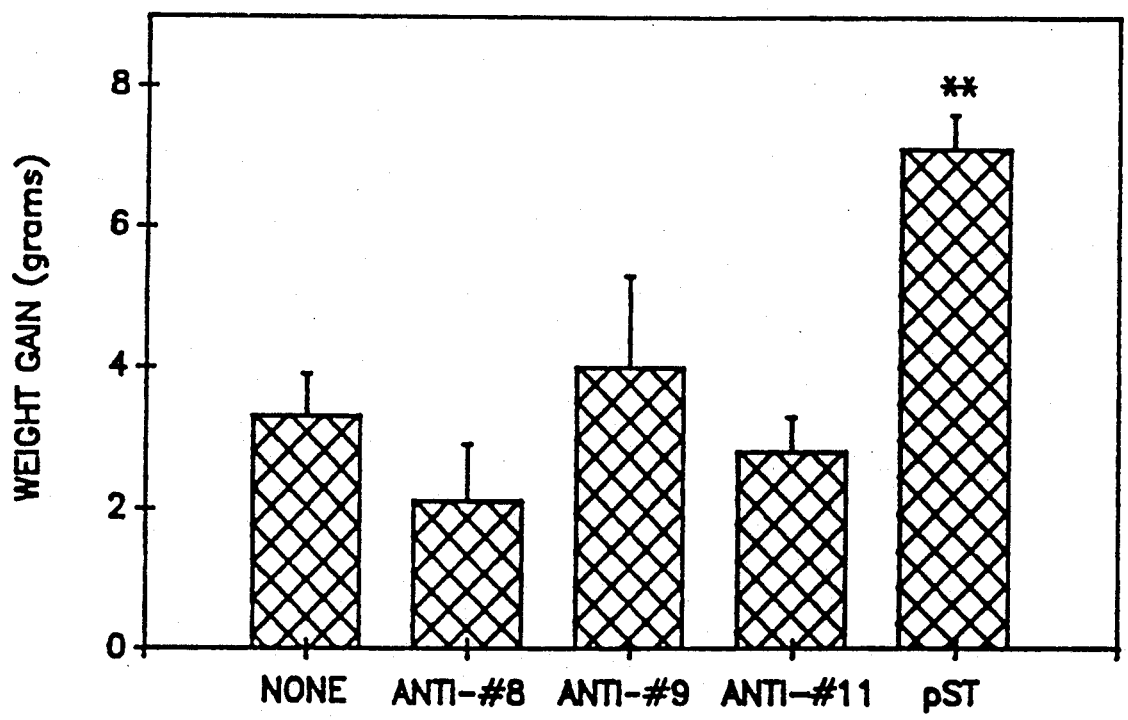
FIG. 8 depicts the effect on the growth of hypophysectomized rats treated with pST alone or swine antibodies to pST peptides alone (not combined with pST).

This enhancing effect of swine antibodies seen above results only in conjunction with pST, because these antibodies do not stimulate hypox-rats to grow when given by themselves without pST (FIG. 8). As anticipated, pST alone promotes the growth of hypox-rats.

8. Enhancement of Growth Performance by Rabbit Antibodies

Figure 11:
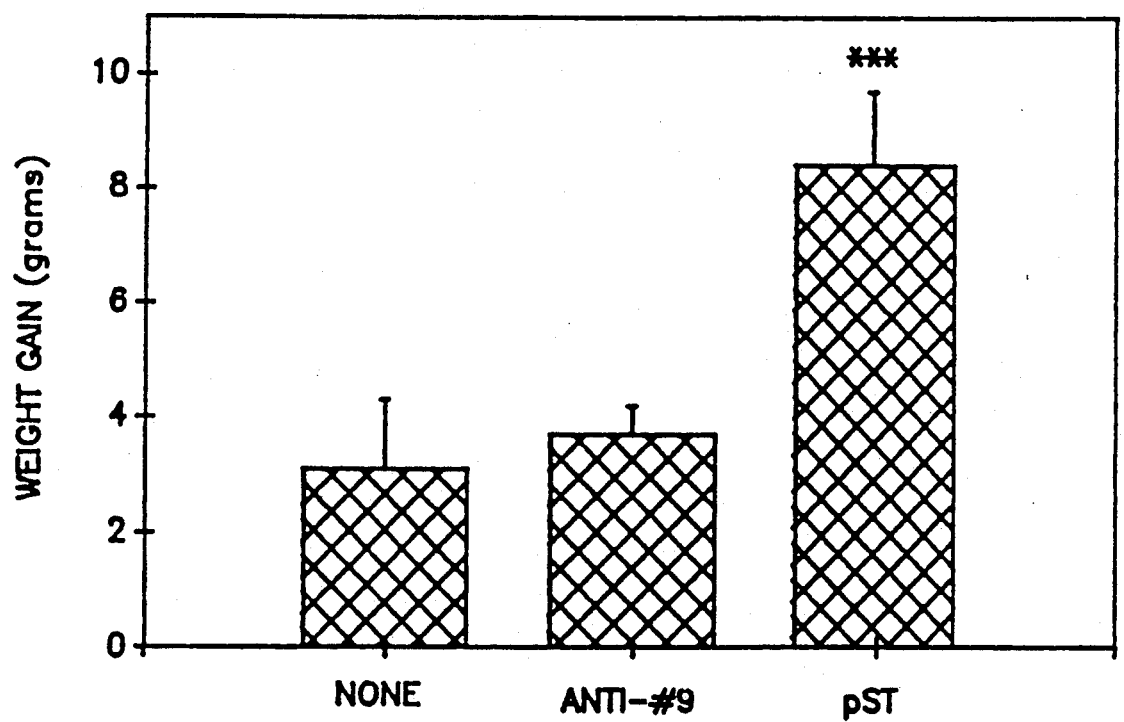
FIG. 11 depicts the effect on the growth of hypophysectomized rats treated with pST alone or rabbit antibodies to pST peptides alone (not combined with pST).

Rabbit antibodies to pST peptides are similarly prepared and tested in hypox-rats. Each antibody tested is mixed separately with pST (5 μg) for one hour at room temperature and injected subcutaneously to rats for four consecutive days. Data from two separate experiments are summarized in FIGS. 9 and 10. It is clear that rabbit antibodies to pST peptide #9 (aa=110–118) significantly potentiate the effect of pST in promoting the growth. The remainders, including normal rabbit Ig, antibody to pST and antibodies to other peptide sequences, are less effective. Furthermore, rabbit antibodies to peptide #9 do not affect the growth of the hypox-rats when administered in the absence of pST (FIG. 11). Again, pST alone stimulates a significant enhancement of growth in these animals.

EXAMPLE 2

1. Generation Of Monoclonal Antibodies To pST Peptides

Balb/C mice, 6 to 10 weeks of age, are purchased from Charles River Breeding Laboratories, Wilmington, Mass. These mice are immunized with 100 μg KLH conjugated with one of peptides #8, 9 or 11, prepared in accordance with the procedure of Example 1, in the presence of Freund's complete adjuvant. The animals are boostered with 50 μg of the same peptide every three weeks thereafter. Their spleens are removed three days after the last boosting and single cell suspensions of lymphocytes are prepared. These lymphocytes are fused with PS2/0 mouse myeloma cells lacking hypoxanthine phosphoribosyl transferase (HPRT-negative) with 50% polyethylene glycol, suspended in Dulbecco's minimum essential medium containing 20% fetal calf serum, 0.175 mg/ml aminopterin, 13.6 mg/ml hypoxanthine, 3.88 mg/ml thymidine and 50 mg/ml gentamicin, and finally dispensed in 96-well culture plates. After culturing for 10–14 days, supernatants of the hybridomas who survive due to the HPRT-positive phenotype of the lymphocytes are collected for antibody screening in a solid-phase ELISA. Those determined to produce appropriate antibodies are further subcloned by a limited dilution procedure. The clones so selected are injected intraperitoneally into Balb/C mice which are primed with pristane for the production of the antibody-containing ascites.

2. Preparation Of Monoclonal Antibody

Ascites are collected from the peritoneal cavities of mice and Ig is purified by 50% ammonium sulfate precipitation technique. Alternatively, samples are diluted to 50% with binding buffer (3M NaCl, 1.5M glycine, pH 8.9) and loaded onto a preparative Protein A Superose HR 16/5 column on a FPLC system (Pharmacia, Piscataway, N.J.). The non-Ig fraction is eluted from the column with the binding buffer. The bound Ig is subsequently collected by rinsing the column with 0.1M citric acid, pH 3. The bound Ig is immediately neutralized to pH 7–8 with 2M Tris buffer, pH 8.2. Antibody prepared by both procedures is extensively dialyzed against phosphate buffered saline (PBS), concentrated by ultrafiltration (Amicon, Danvers, Mass.), aliquoted, and finally stored at −20° C. until use.

The monoclonal antibody titer level is assayed using the ELISA procedure described in Example 1.

The immunoreactivity of and the enhancement of growth performance by the monoclonal antibodies of this Example are determined using the procedures described in Example 1.

We claim:

1. A peptide consisting essentially of nine amino acids, said peptide having the amino acid sequence Tyr-Glu-Lys-Leu-Lys-Asp-Leu-Glu-Glu, which corresponds to amino acid residues 110–118 of porcine somatotropin (pST).

2. A modified peptide comprising a peptide according to claim 1 wherein the peptide is linked to a carrier.

3. A modified peptide according to claim 2 wherein the carrier is keyhole limpet haemocyanin.

* * * * *